(12) United States Patent
Neumann (10) Patent No.: US 11,776,020 B2
(45) Date of Patent: Oct. 3, 2023

(54) METHODS AND SYSTEMS FOR MULTI-FACTORIAL PHYSIOLOGICALLY INFORMED REFRESHMENT SELECTION USING ARTIFICIAL INTELLIGENCE

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 652 days.

(21) Appl. No.: 16/864,866

(22) Filed: May 1, 2020

(65) Prior Publication Data

US 2021/0342706 A1    Nov. 4, 2021

(51) Int. Cl.
| | | |
|---|---|---|
| *G06Q 30/00* | (2023.01) | |
| *G06Q 30/0282* | (2023.01) | |
| *H04L 67/52* | (2022.01) | |
| *G06Q 30/0601* | (2023.01) | |
| *G16H 20/60* | (2018.01) | |
| *G16H 50/70* | (2018.01) | |
| *G06Q 50/12* | (2012.01) | |
| *G06F 18/214* | (2023.01) | |

(52) U.S. Cl.
CPC ....... *G06Q 30/0282* (2013.01); *G06F 18/214* (2023.01); *G06Q 30/0631* (2013.01); *G06Q 30/0639* (2013.01); *G06Q 50/12* (2013.01); *G16H 20/60* (2018.01); *G16H 50/70* (2018.01); *H04L 67/52* (2022.05)

(58) Field of Classification Search
CPC .............. G06Q 30/0239; G06Q 50/12; G06Q 30/0282; G06Q 30/0631; G06Q 30/0639; G16H 50/70; G16H 20/60; H04L 67/52; G06K 9/6256; G06V 10/774; G06V 30/19147
See application file for complete search history.

(56) References Cited

U.S. PATENT DOCUMENTS

| | | |
|---|---|---|
| 8,787,979 B2 | 7/2014 | Shen |
| 2004/0204950 A1 | 10/2004 | Vlahos |
| 2008/0052639 A1 | 3/2008 | Chun |

(Continued)

FOREIGN PATENT DOCUMENTS

| | | | |
|---|---|---|---|
| CN | 102780788 A | * | 11/2012 |
| WO | 2016050958 | | 4/2016 |

*Primary Examiner* — Alvin L Brown
(74) *Attorney, Agent, or Firm* — CALDWELL INTELLECTUAL PROPERTY LAW (57) ABSTRACT

A system for multi-factorial physiologically informed refreshment selection using artificial intelligence, the system comprising a computing device, the computing device designed and configured to retrieve a biological extraction pertaining a user, wherein the biological extraction contains an element of user data; select, a nutritional machine-learning model using the biological extraction; determine a geolocation of the user; identify a provider located within the geolocation of the user, wherein the provider generates a plurality of refreshment possibilities; determine the compatibility of the plurality of refreshment possibilities utilizing the biological extraction and the nutritional model; and display the compatibility of the plurality of refreshment possibilities.

19 Claims, 7 Drawing Sheets

(56) References Cited

U.S. PATENT DOCUMENTS

| | | |
|---|---|---|
| 2010/0257050 A1 | 10/2010 | Lee |
| 2013/0311913 A1 | 11/2013 | McCoy et al. |
| 2016/0351072 A1 | 12/2016 | Nusbaum |
| 2019/0163710 A1 | 5/2019 | Haghighat Kashani et al. |
| 2020/0302086 A1* | 9/2020 | Post .................. G06F 21/33 |
| 2021/0201231 A1* | 7/2021 | Mimassi ............. G06Q 50/12 |

* cited by examiner

METHODS AND SYSTEMS FOR MULTI-FACTORIAL PHYSIOLOGICALLY INFORMED REFRESHMENT SELECTION USING ARTIFICIAL INTELLIGENCE

FIELD OF THE INVENTION

The present invention generally relates to the field of artificial intelligence. In particular, the present invention is directed to methods and systems for multi-factorial physiologically informed refreshment selection using artificial intelligence.

BACKGROUND

Informed refreshment selection can be challenging. Frequently, users are confused due to the vast multitude of ever changing recommendations provided. Information containing individual custom recommendations remains to be seen.

SUMMARY OF THE DISCLOSURE

In an aspect, a system for multi-factorial physiologically informed refreshment selection using artificial intelligence the system comprising a computing device, the computing device designed and configured to retrieve a biological extraction pertaining a user, wherein the biological extraction contains an element of user data; select, a nutritional machine-learning model using the biological extraction; determine a geolocation of the user; identify a provider located within the geolocation of the user, wherein the provider generates a plurality of refreshment possibilities; determine the compatibility of the plurality of refreshment possibilities utilizing the biological extraction and the nutritional model; and display the compatibility of the plurality of refreshment possibilities.

In an aspect, a method of multi-factorial physiologically informed refreshment selection using artificial intelligence the method comprising retrieving by a computing device, a biological extraction pertaining a user, wherein the biological extraction contains an element of user data; selecting by the computing device, a nutritional machine-learning model using the biological extraction; determining by the computing device, a geolocation of the user; identifying by the computing device, a provider located within the geolocation of the user, wherein the provider generates a plurality of refreshment possibilities; determining by the computing device, the compatibility of the plurality of refreshment possibilities utilizing the biological extraction and the nutritional model; and displaying by the computing device, the compatibility of the plurality of refreshment possibilities.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for multi-factorial physiologically informed refreshment selection using artificial intelligence. In an embodiment, a biological extraction is utilized to select a nutritional machine-learning model. A nutritional machine-learning model is utilized in combination with a geolocation of a user to identify providers located within the geolocation and evaluate the compatibility of refreshment possibilities offered by the providers.

Figure 1:
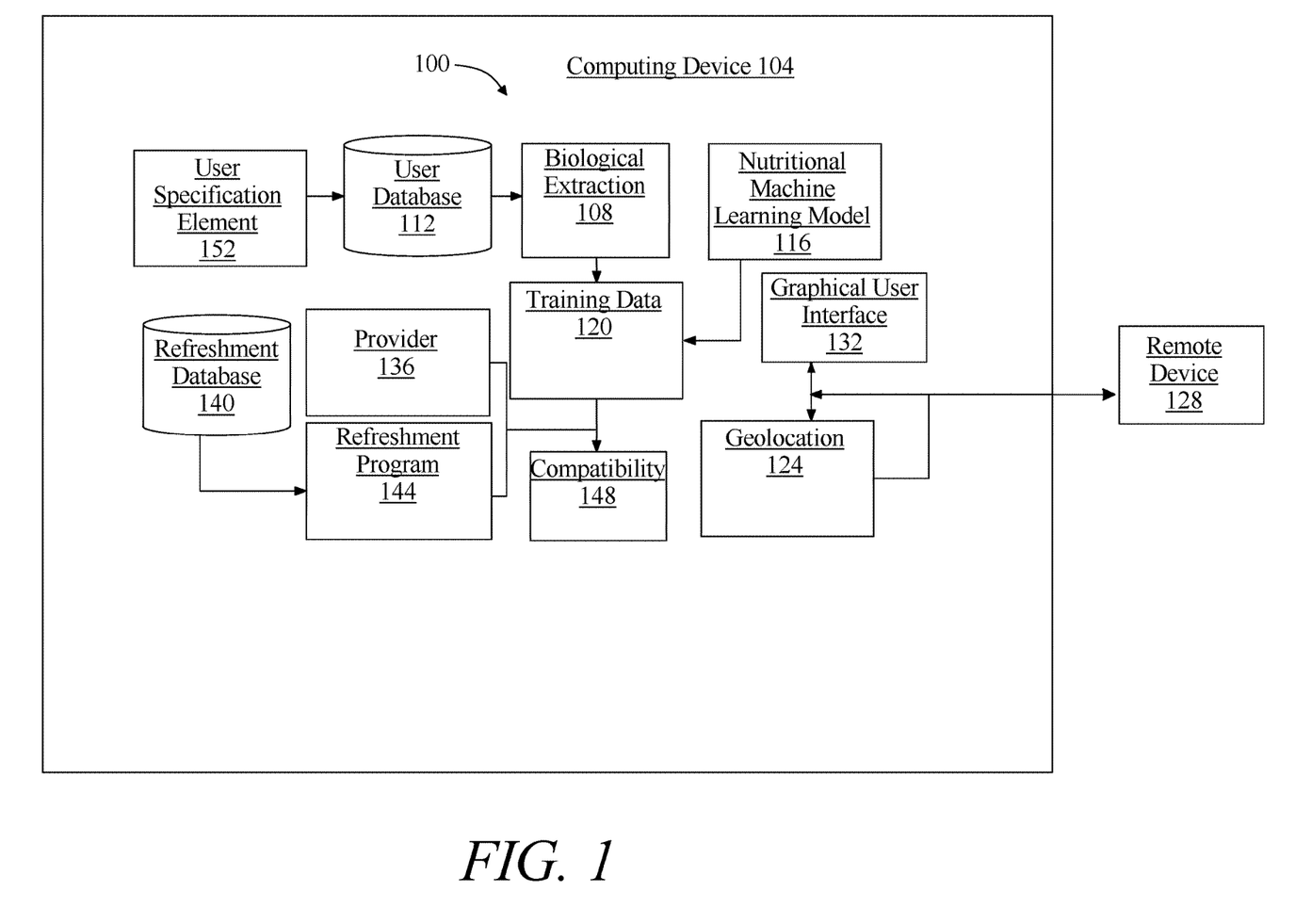
FIG. 1 is a block diagram illustrating an exemplary embodiment of a system for multi-factorial physiologically informed refreshment selection using artificial intelligence.

Referring now to FIG. 1, an exemplary embodiment of a system 100 for multi-factorial physiologically informed refreshment selection using artificial intelligence is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first location and a second computing device 104 or cluster of computing devices 104 in a second location. Computing device 104 may include one or more computing devices 104 dedicated to data storage, security, distribution of traffic for load balancing, and the like. Computing device 104 may distribute one or more computing tasks as described below across a plurality of computing devices 104 of computing device 104, which may operate in parallel, in series, redundantly, or in any other manner used for distribution of tasks or memory between computing devices 104. Computing device 104 may be implemented using a "shared nothing" architecture in which data is cached at the worker, in an embodiment, this may enable scalability of system 100 and/or computing device 104.

Continuing to refer to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 is configured to retrieve a biological extraction 108 pertaining a user, wherein the biological extraction 108 contains an element of user data. A "biological extraction," as used in this disclosure, is an element of data including at least an element of user data. As used in this disclosure, "user data" is any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. A biological extraction 108 may include any of the biological extraction 108 as disclosed in U.S. Nonprovisional application Ser. No. 16/659,817, filed on Oct. 22, 2019, and entitled "METHODS AND SYSTEMS FOR IDENTIFYING COMPATIBLE MEAL OPTIONS," the entirety of which is incorporated herein by reference. In an embodiment, a biological extraction 108 pertaining to a user may be stored in a user database 112. User database 112 may include any data structure for ordered storage and retrieval of data, which may be implemented as a hardware and/or software module. A user database 112 may be implemented, without limitation, as a relational database, a key-value retrieval datastore such as a NOSQL database, or any other format or structure for use as a datastore that a person skilled in the art would recognize as suitable upon review of the entirety of this disclosure.

With continued reference to FIG. 1, computing device 104 is configured to select a nutritional machine-learning model 116 using a biological extraction 108. A "nutritional machine-learning model," as used in this disclosure, is a machine-learning model that utilizes a biological extraction 108 and/or a plurality of refreshment possibilities as an input, and outputs compatibilities of the plurality of refreshment possibilities. A machine-learning model, as used herein, is a mathematical representation of a relationship between inputs and outputs, as generated using any machine-learning process including without limitation any process as described herein, and stored in memory; an input is submitted to a machine-learning model once created, which generates an output based on the relationship that was derived. Selection of a nutritional machine-learning model 116 may include selection of a machine-learning model, a training data 120 set to be used in a machine-learning algorithm and/or to produce a machine-learning model, and/or a machine-learning algorithm such as a supervised machine-learning algorithm, an unsupervised machine-learning model, and/or a lazy learning algorithm. In an embodiment, computing device 104 and/or one or more other devices, components, and/or modules of system 100 may train nutritional machine-learning model using training data 120; computing device 104 and/or one or more other devices, components, and/or modules of system 100 may generate nutritional machine-learning model by executing any machine-learning algorithm as described herein using training data 120 to perform the execution.

With continued reference to FIG. 1, nutritional machine-learning model 116 may be trained using training data 120 that may be stored in user database 112. "Training data," as used in this disclosure, is data containing correlations that a machine-learning process may use to model relationships between two or more categories of data elements. Training data 120 may be formatted and/or organized by categories of data elements, for instance by associating data elements with one or more descriptors corresponding to categories of data elements. Alternatively or additionally, training data 120 may include one or more elements that are not categorized; that is, training data 120 may not be formatted or contain descriptors for some elements of data. In an embodiment, training data 120 may come from past interactions of a user with system 100, as described below in more detail.

With continued reference to FIG. 1, computing device 104 may select a nutritional machine-learning model 116 associated with a particular biological extraction 108. For instance and without limitation, a biological extraction 108 that contains a microbiome sample, may be utilized to select a nutritional machine-learning model 116 associated with the same microbiome sample. In yet another non-limiting example, a biological extraction 108 that contains a urine sample analyzed for one or more neurotransmitter levels may be utilized to select a nutritional machine-learning model 116 associated with the same urinalysis. In yet another non-limiting example, a biological extraction 108 that contains a user's response to a questionnaire may be utilized to select a nutritional machine-learning model 116 associated with the same questionnaire. Computing device 104 is configured to select a nutritional machine-learning model 116 utilizing previous user refreshment data. "Previous user refreshment data," as used in this disclosure, is data describing any previous interactions between a user and system 100. For instance and without limitation, previous user refreshment data may contain previous refreshment possibilities that a user selected. In yet another non-limiting example, previous user refreshment data may include any preferences of a user in regard to refreshment possibilities. In an embodiment, computing device 104 retrieves and/or looks up user refreshment data from user database. This may be performed, for example by generating a search query and utilizing the search query to locate and/or extract user refreshment data from a particular date or period in time. Previous user refreshment data may be stored in user database 112. In an embodiment, previous user refreshment data may be utilized to train nutritional machine-learning model 116.

With continued reference to FIG. 1, computing device 104 is configured to determine a geolocation 124 of a user. A "geolocation of a user," as used in this disclosure, is an identification of a real-world geographical location related to the user. A geolocation 124 of a user may be obtained from a radar source, a mobile device, and/or internet connected device location. A geolocation 124 of a user may include a global positioning system (GPS) of a user. A geolocation 124 of a user may include geographic coordinates that specify the latitude and longitude of a location where a user currently is located, and/or a location where a user may be located in the future. In an embodiment, a geolocation 124 may specify the location where a user is located at the present moment. For example, a geolocation 124 may place the user as currently being located in Dallas, Tex. In an embodiment, a geolocation 124 may specify a location where a user may be located at some point in the future. For example, a geolocation 124 may specify that a user who currently resides in Billings, Mont. may be located in Anchorage, Ak. for the next three days on a business trip. In yet another non-limiting example, a geolocation 124 may specify that a user who lives and works in the West End of Austin, Tex. may be located in the East End of Austin, Tex. during lunchtime.

With continued reference to FIG. 1, computing device 104 may receive a geolocation 124 of a user entered from a remote device 128 operated by a user. A remote device 128 may include without limitation, a display in communication with computing device 104, where a display may include any display as described herein. Remote device 128 may include an additional computing device, such as a mobile device, laptop, desktop, computer, and the like. In an embodiment, computing device 104 may receive an input containing a geolocation 124 of a user utilizing any network methodology as described herein. In an embodiment, computing device 104 may contain a graphical user interface 132, where a user may enter information about a user's geolocation 124. Graphical user interface 132 may include without limitation, a form or other graphical element having display fields, where one or more elements of information may be displayed. Graphical user interface 132 may include sliders or other user inputs that may permit a user to indicate a geographical location where the user is currently located and/or where the user will be located in the future. In an embodiment, graphical user interface 132 may display an interactive map, that may allow a user to touch and/or select a geographical location pertaining to the user. Graphical user interface 132 may include free form textual entries, where a user may be able to type in a geographical location.

With continued reference to FIG. 1, computing device 104 is configured to identify a provider 136 located within a geolocation 124 of a user. A "provider," as used in this disclosure, is any provider of dietary nutrition. A provider 136 may include a restaurant, such as a café, bistro, grill, tavern, cafeteria, diner, eatery, food hall, and the like. A provider 136 may include a sit down restaurant, a takeout restaurant, and the like. A provider 136 may include a chain restaurant or an independently owned restaurant. A provider 136 may include a company that prepares meals. A provider 136 may include any online and/or in person store that sells groceries. A provider 136 may include a grocery store that sells meal kits, and/or meals. A provider 136 may include a chef or cook who prepares meals at home for sale, or in a commercialized kitchen. A provider 136 generates a plurality of refreshment possibilities. A "refreshment possibility," as used in this disclosure, is any food, meal, and/or drink prepared for eating. A refreshment possibility may include any item consumed by a human being. A refreshment possibility may include a meal such as a breakfast option that contains organic Greek yogurt topped with grain free granola and berries. A refreshment possibility may include a snack such as a cheese platter containing cheese, crackers, fig spread, and grapes. A refreshment possibility may include a beverage such as hot chocolate or a mint julep. In an embodiment, a provider 136 may make available a plurality of refreshment possibilities available for purchase, such as by posting a menu online and/or posted in print at the location of the provider 136. In an embodiment, a provider 136 may prepare and create different refreshment possibilities at different times of the day and/or week. For example, a provider 136 may offer fifteen different refreshment possibilities for breakfast, and ten different refreshment possibilities for lunch. A provider 136 may offered different refreshment possibilities on different days of the week. For example, a provider 136 may offer shrimp scampi as refreshment possibility only on Wednesday nights, and chicken parmesan as a refreshment possibility only on Friday nights. Computing device 104 may communicate with one or more computing devices operated by provider 136 to obtain updated refreshment possibilities. One or more refreshment possibilities may be stored in refreshment database 140. Refreshment database 140 may be implemented as any data structure suitable for use as user database 112 as described above in more detail. In an embodiment, refreshment database 140 may be updated in real time to contain updated refreshment possibilities from various provider 136 utilizing any network methodology as described herein.

With continued reference to FIG. 1, computing device 104 is configured to receive a user input containing an element of user geolocation 124 data. Computing device 104 may receive a user input from a remote device 128 operated by a user, utilizing any network methodology as described herein. Computing device 104 may receive a user input containing an element of user geolocation 124 data describing a user's current geolocation 124. In yet another non-limiting example, computing device 104 may receive a user input containing an element of user geolocation 124 data describing a particular location where a user will be located at a time in the future. For example, a user input containing an element of user geolocation 124 data may specify that a user will be traveling to Denver, Colo. for three days later in the week. Computing device 104 is configured to locate provider 136 located within a specified distance of an element of user geolocation 124 data. Computing device 104 may locate provider 136 within a specified distance such as by consulting refreshment database 140. In an embodiment, a user may enter a preference that may be stored in user database 112, specifying a distance a user is willing to travel to from a user geolocation 124 to a provider 136. For example, a user may enter an input into user database 112 specifying that the user prefers to not travel more than five miles from a specified geolocation 124 to locate provider 136. In an embodiment, a user may provide a specified distance with an element of user geolocation 124 data, as distances a user may be willing to travel may vary based on a particular geolocation 124. For example, a user may prefer to travel up to twenty five miles from user's home in Kansas City, Mo., but a user may prefer to only travel a distance of five city blocks when the user is traveling and located in New York City for work.

With continued reference to FIG. 1, computing device 104 is configured to locate a provider 136 located within a geolocation 124 as a function of a refreshment program. A "refreshment program," as used in this disclosure, is a description of any meals offered and/or served by a provider 136. A refreshment program may specify specific meals that a provider 136 may offer, such as breakfast, and lunch service. A refreshment program may specify certain times of the day that refreshment possibilities are available, such as snacks that are available for purchase between 4 pm-6 pm, and dinner that is available for purchase between 6:30 pm-10:30 pm. Information pertaining to refreshment programs for various provider 136 may be stored in refreshment database 140. Computing device 104 may consult refreshment database 140 to determine refreshment programs that are available for provider 136 located within a certain geographical area. Computing device 104 receives from a provider 136 a current refreshment program. A "current refreshment program," as used in this disclosure, is any present refreshment program offered by a provider 136. Computing device 104 may receive a current refreshment program at timed intervals. For example, computing device 104 may receive a current refreshment program from a provider 136 every Friday, containing an updated refreshment program for the following week. In yet another non-limiting example, computing device 104 may receive a current refreshment program only when a change is made to a refreshment program, which may be updated and shared with computing device 104. Computing device 104 may receive a current refreshment program utilizing any network methodology as described herein.

With continued reference to FIG. 1, computing device 104 is configured to determine the compatibility of a plurality of refreshment possibilities utilizing a biological extraction 108 and a nutritional model. A "compatibility," as used in this disclosure, is any data, including any numerical, character, and/or symbolic data specifying how likely a refreshment possibility will be tolerated by a user's body. In an embodiment, a compatibility 148 may be generated on a numerical score, such as on a range from 0 to 100. In such an instance, a score such as 0 would indicate a refreshment possibility will not be tolerated by a user's body, while a score such as 100 would be well tolerated by a user's body. Computing device 104 determines the compatibility 148 of a plurality of refreshment possibilities by utilizing a user's biological extraction 108, and a plurality of refreshment possibilities as inputs into a nutritional model and outputting a compatibility 148 of each of the plurality of refreshment possibilities. Computing device 104 may use training data 120 to train a nutritional model. In an embodiment, data used to train a nutritional model may come from previous interactions of a user and system 100. For example, user database 112 may store any previously calculated compatible refreshment possibilities. In yet another non-limiting example, computing device 104 may store within user database 112 any previous health information about a user, such as any eating habits, food preferences, dietary restrictions, food allergies, food intolerances, foods a user does not enjoy eating, foods a user prefers eating and the like.

With continued reference to FIG. 1, computing device 104 is configured to retrieve a recent refreshment selection, wherein the recent refreshment selection identifies a consumed refreshment. A "recent refreshment selection," as used in this disclosure, is any refreshment possibility that a user selected and consumed. In an embodiment, one or more recent refreshment selections may be stored in user database 112. Computing device 104 determines the compatibility 148 of a plurality of refreshment possibilities using a recent refreshment selection. Computing device 104 may utilize a recent refreshment selection as an input to nutritional machine-learning model 116. In yet another non-limiting example, computing device 104 may evaluate one or more ingredients contained within a recent refreshment selection to determine the compatibility 148 of a plurality of refreshment possibilities, to ensure that a user obtains enough nutrients and/or doesn't consume an excess amount of ingredients that may be harmful to a user. An "ingredient," as used in this disclosure, is any food, substance, and/or component contained within a refreshment possibility. For example, a refreshment possibility such as chicken piccata may contain ingredients that include chicken breast, sea salt, ground pepper, all-purpose flour, unsalted butter, extra-virgin olive oil, lemon juice, chicken stock, brined capers, and fresh parsley. Computing device 104 may evaluate ingredients contained within a recent refreshment selection such as chicken piccata to ensure that a user with a biological extraction 108 that shows the user has high cholesterol, does not consume too many meals that contain excess amounts of butter. Computing device 104 may evaluate ingredients contained within chicken piccata, determine the chicken piccata has butter, and determine that refreshment possibilities that contain butter from a plurality of refreshment possibilities will not be ranked as highly compatible as any refreshment possibilities that do not contain butter. In an embodiment, a recent refreshment selection may be examined to determine how recent in time it may be, to determine how much weight it may have on a compatibility. For instance and without limitation, a refreshment selection that was consumed one day ago may have more of an impact on a compatibility as compared to a refreshment selection that was consumed three weeks previously.

With continued reference to FIG. 1, computing device 104 is configured to determine the compatibility 148 of refreshment possibilities for a first provider 136. A "first provider," as used in this disclosure, is any provider 136 who is selected first. In an embodiment, computing device 104 may determine the compatibility 148 of a plurality of refreshment possibilities offered by a first provider 136. For example, computing device 104 may evaluate a current refreshment program offered by a first provider 136. Computing device 104 may utilize the compatibility 148 of a plurality of refreshment possibilities to determine the compatibility 148 of a plurality of refreshment possibilities for a second provider 136. For example, computing device 104 may determine that a first refreshment possibility offered by a first provider 136 such as buttermilk pancakes with maple syrup and fresh fruit are moderately compatible for a user. In such an instance, computing device 104 may determine that buttermilk pancakes with maple syrup and berries offered by a second provider 136 are also moderately compatible, based on the buttermilk pancakes with maple syrup and fresh fruit being moderately compatible for the first provider 136. In yet another non-limiting example, computing device 104 may determine that a first refreshment possibility that contains avocado toast offered by a first provider 136 is not compatible for a user because the user has a mild food intolerance to avocado. However, computing device 104 may utilize the information to determine that enchiladas served with a side containing one slice of avocado may be moderately tolerant for the user, because the one slice of avocado if consumed will not be enough to trigger a full intolerance reaction.

With continued reference to FIG. 1, computing device 104 determines the compatibility 148 of a plurality of refreshment possibilities utilizing an ingredient list for each of the plurality of refreshment possibilities. An "ingredient list," as used in this disclosure, is any compilation of ingredients used to prepare a refreshment possibility. An ingredient list may be obtained from a provider 136 and stored within refreshment database 140. Computing device 104 updates ingredient lists on a timed interval from a provider 136. For example, a provider 136 may agree to update an ingredient list once per week to account for ingredients that a provider 136 may or may not be able to obtain during the following week. In yet another non-limiting example, a provider 136 may update an ingredient list once per day, to account for different refreshment possibilities that may be available each day. For example, ingredients that a provider 136 can obtain may vary based on current world events, market demands, consumer appeal, seasonal availability of ingredients, and various other factors.

With continued reference to FIG. 1, computing device 104 is configured to determine an incompatible refreshment possibility. An "incompatible refreshment possibility," as used in this disclosure, is any refreshment possibility that will not be well tolerated by a user's body. In an embodiment, an incompatible refreshment possibility may meet a specific numerical threshold to be considered incompatible. For instance and without limitation, refreshment possibilities that are evaluated on a scale of 0 to 100 for compatibility 148 as described above in more detail, may consider that all refreshment possibilities scored from 0 to 50 are considered incompatible. Computing device 104 may determine an incompatible refreshment possibility utilizing nutritional machine-learning model. For example, nutritional machine-learning model may determine that a refreshment possibility is incompatibly, because of the output compatibility generated by nutritional machine-learning model. For instance and without limitation, nutritional machine-learning model may determine that a refreshment possibility containing fried chicken has a very low compatibility for a user, and thus computing device 104 may identify the refreshment possibility as an incompatible refreshment possibility. Compatibility and/or incompatibility 148 of refreshment possibilities may flux and vary over time. For example, a refreshment possibility that contains a lot of dairy ingredients such as fresh ice cream may be considered an incompatible refreshment possibility for a user with respiratory syncytial virus (RSV), while the refreshment possibility for fresh ice cream may be considered moderately compatible for the user once the user has recovered from RSV. Computing device 104 is configured to propose a modification to a refreshment possibility to improve compatibility 148. A "modification," as used in this disclosure, is any suggested substitution for one or more ingredients contained within a refreshment possibility. For example, computing device 104 may determine that a taco salad that contains sour cream may not be very compatible for a user because of a high amount of saturated fat contained within sour cream. In such an instance, computing device 104 may determine a modification that replaces sour cream with Greek yogurt may modify the taco salad to improve the compatibility of the taco salad. One or more lists of ingredients that can be substituted and/or replaced for one another may be contained within refreshment database 140. For example, a modification such as substituting ground turkey in lieu of ground beef to reduce cholesterol consumption may be stored within refreshment database 140. In an embodiment, computing device 104 may propose a modification using a machine-learning algorithm, including any of the machine-learning algorithms as described herein. For example, computing device 104 may utilize an ingredient as an input to a machine-learning algorithm and output one or more modifications.

With continued reference to FIG. 1, computing device 104 is configured to retrieve a user specification element. A "user specification element," as used in this disclosure, is any user response and/or preference of a user regarding refreshment possibilities. A user specification element 152 may be based on a questionnaire completed by a user containing information regarding a user's behaviors, foods and/or ingredients that a user likes to eat, foods and/or ingredients that a user does not like to consume, and the like. A user specification element may be stored within user database 112. Computing device 104 determines the compatibility 148 of a plurality of refreshment possibilities utilizing a user specification element 152. For example, a user specification element 152 that describes a user's distaste for eggs, may be utilized by computing device 104 to determine a refreshment possibility such as an omelet may be ranked as less compatible as compared to a refreshment possibility such as a bowl of oatmeal topped with fresh berries and walnuts.

With continued reference to FIG. 1, computing device 104 is configured to display a compatibility of a plurality of refreshment possibilities. Computing device 104 may display a compatibility 148 of a plurality of refreshment possibilities on graphical user interface 132. In an embodiment, computing device 104 may transmit a compatibility 148 of a plurality of refreshment possibilities to remote device 128 operated by a user. In an embodiment, computing device 104 may display a number indicating a compatibility of a refreshment possibility, a qualitative statement containing an indication of compatibility such as high, medium, or low, a photograph of a refreshment possibility containing an indication of compatibility and the like.

Figure 2:
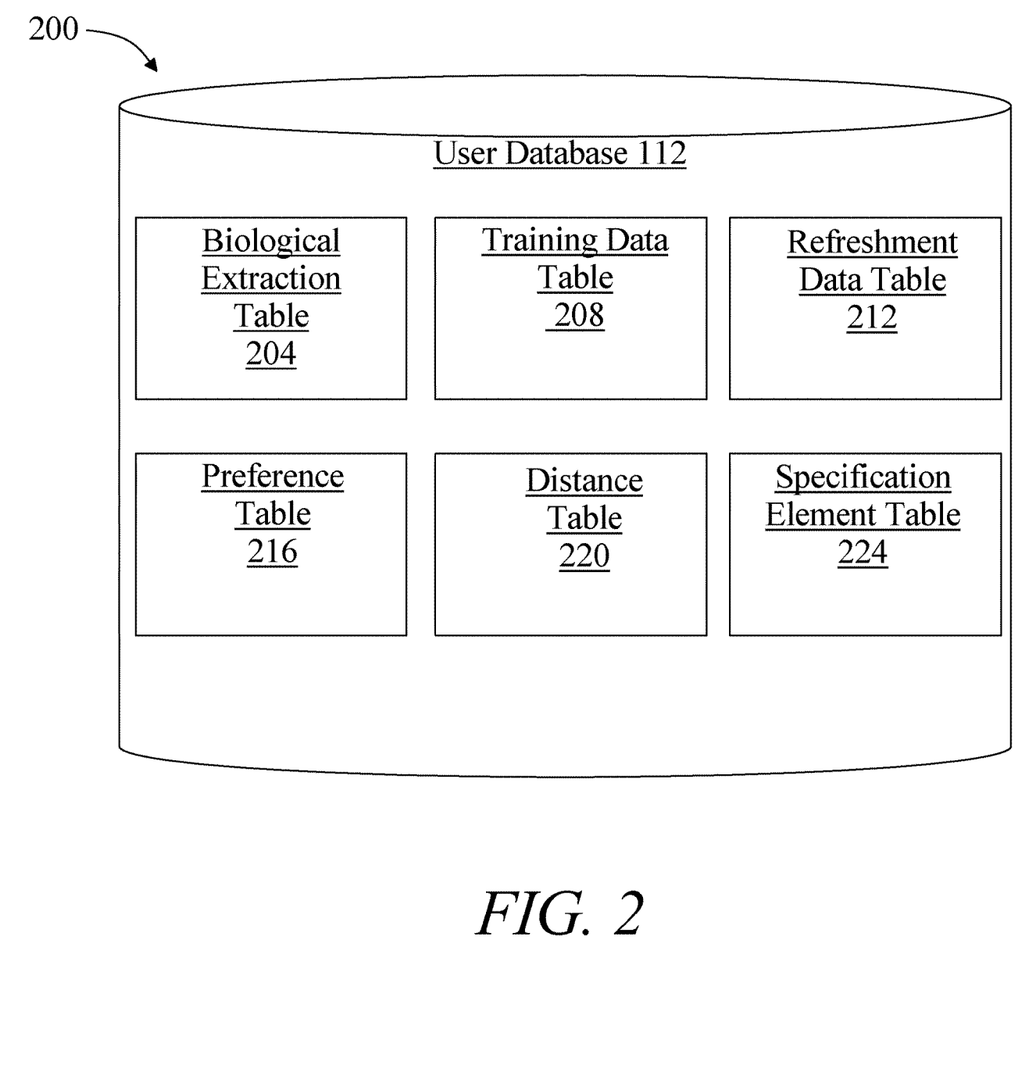
FIG. 2 is a block diagram illustrating an exemplary embodiment of a user database.

Referring now to FIG. 2, an exemplary embodiment 200 of user database 112 is illustrated. User database 112 may be implemented as any data structure as described above in more detail in reference to FIG. 1. One or more tables contained within user database 112 may include biological extraction table 204; biological extraction table 204 may contain one or more biological extractions pertaining to a user. For instance and without limitation, biological extraction table 204 may contain a blood sample analyzed for intracellular and extracellular nutrient levels of calcium, magnesium, iron, and zinc. One or more tables contained within user database 112 may include training data table 208; training data table 208 may contain one or more training sets. For instance and without limitation, training data table 208 may contain a training set generated from one or more user inputs and one or more previous user interactions with system 100 as described above in more detail in reference to FIG. 1. One or more tables contained within user database 112 may include refreshment data table 212; refreshment data table 212 may include previous user refreshment data. For instance and without limitation, refreshment data table 212 may contain a description of a meal that a user recently consumed that included a turkey burger served on a bed of lettuce with a side of parsnip fries. One or more tables contained within user database 112 may include preference table 216; preference table 216 may include one or more user preferences in regarding to refreshment possibilities. For instance and without limitation, preference table 216 may contain a user preference that specifies that a user prefers to eat dinner no later than 6 pm each night. One or more tables contained within user database 112 may include distance table 220; distance table 220 may contain information pertaining to any distance that a user prefers to locate provider 136 within based on a user's geolocation 124. For instance and without limitation, distance table 220 may specify that a user prefers to locate provider 136 located within a two mile radius of a user's home in Seattle, Wash. One or more tables contained within user database 112 may include specification element table 224; specification element table 224 may contain one or more user specification element 152. For instance and without limitation, specification element table 224 may contain a user specification to not consume any ingredients containing dill weed, as the user does not like the taste of dill weed.

Figure 3:
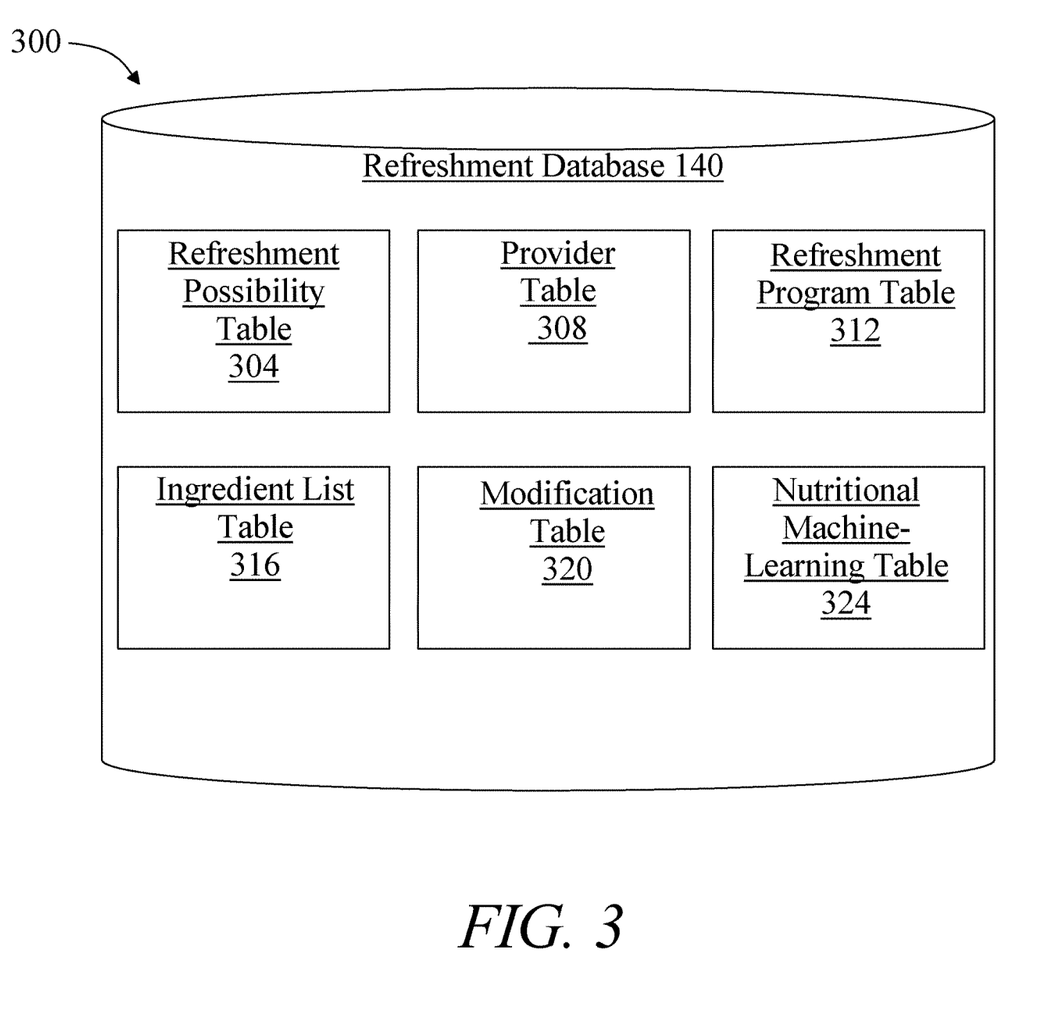
FIG. 3 is a block diagram illustrating an exemplary embodiment of a refreshment database.

Referring now to FIG. 3, an exemplary embodiment 300 of refreshment table is illustrated. Refreshment table may be implemented as any data structure as described above in more detail in reference to FIG. 1. One or more tables contained within refreshment database 140 may include refreshment possibility table 304; refreshment possibility table 304 may include one or more refreshment possibilities offered by one or more provider 136. For instance and without limitation, refreshment possibility table 304 may contain a list of lunch options available at a provider 136 that include a turkey club sandwich, fish tacos, chicken Caesar salad, and grilled salmon with lentils. One or more tables contained within refreshment database may include provider table 308; provider table 308 may include a list of providers 136 located within particular geographical areas. For instance and without limitation, provider table 308 may include a list of providers 136 located in Denver, Colo. One or more tables contained within refreshment database 140 may include refreshment program table 312; refreshment program table 312 may include a list of refreshment programs available at provider 136. For instance and without limitation, refreshment program table 312 may contain a list of providers 136 that offer meals for dinner. One or more tables contained within refreshment database 140 may include ingredient list table 316; ingredient list table 316 may include ingredient lists for provider 136. For instance and without limitation, ingredient list table 316 may contain a list of ingredients contained within a pumpkin spice muffin available at a provider 136 in Savannah, Ga. One or more tables contained within refreshment database 140 may include modification table 320; modification table 320 may include one or more modifications. For instance and without limitation, modification table 320 may contain a modification that indicates one mashed up banana can be substituted for one egg, when a lower cholesterol substitute or an allergy to eggs occurs. One or more tables contained within refreshment database 140 may include nutritional machine-learning table 324; nutritional machine-learning table 324 may contain one or more nutritional machine-learning models. For instance and without limitation, nutritional machine-learning table 324 may contain a supervised nutritional machine-learning model 116.

Figure 4:
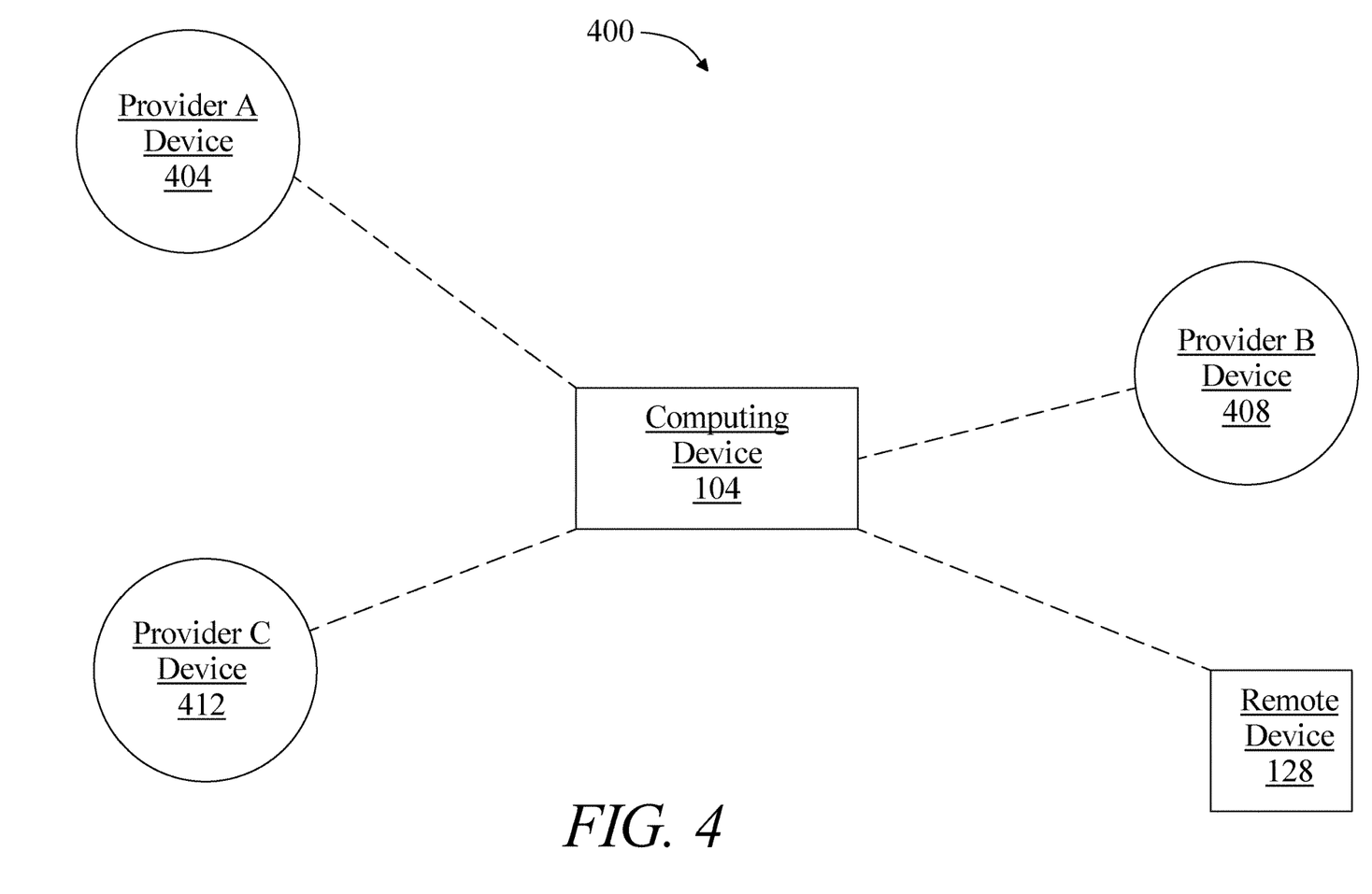
FIG. 4 is a diagrammatic representation illustrating an exemplary embodiment of various providers in communication with computing device.

Referring now to FIG. 4, an exemplary embodiment 400 of a plurality of providers 136 in communication with computing device 104 is illustrated. In an embodiment, provider A device 404 may include any device suitable for use as computing device 104, as described above in more detail in reference to FIG. 1. Provider A device 404 may communicate with computing device 104 utilizing any network methodology as described herein. Provider A device 404 may transmit information to computing device 104 such as currently available refreshment possibilities, current refreshment programs, ingredient lists, modifications, and the like. Computing device 104 may communicate with other provider 136 devices, including for example Provider B device 408 ad Provider C device 412. In an embodiment, Provider A device 404, Provider B device 408, and/or Provider C device 412 may be located within a certain geographical distance and/or location of one another, remote device 128, and/or a geolocation 124 of a user.

Figure 5A:
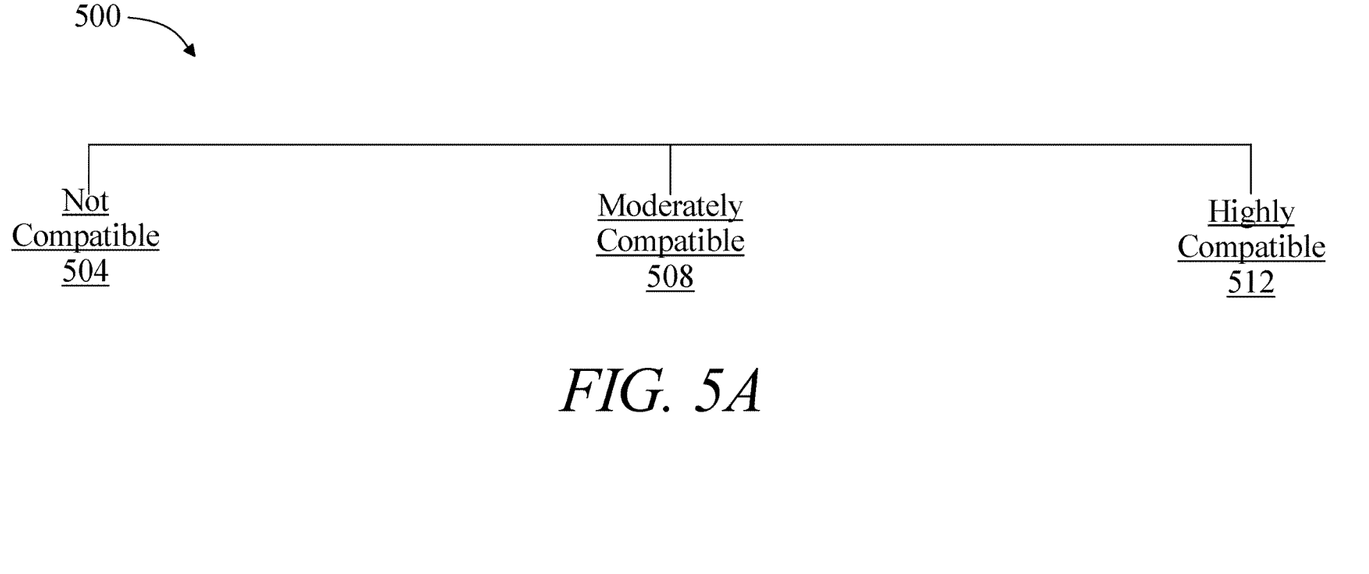
FIGS. 5A-5B are diagrammatic representations illustrating exemplary embodiments of compatibility scales.
Figure 5B:
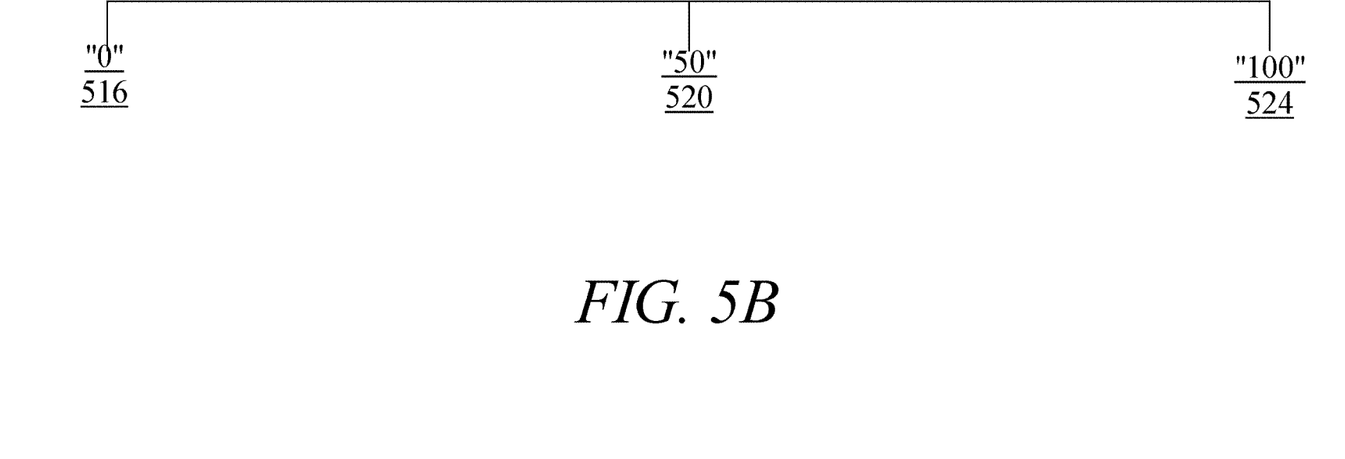

Referring now to FIGS. 5A-5B, an exemplary embodiment 500 of a compatibility scale is illustrated. Referring now to FIG. 5A, refreshment possibility compatibility may be expressed on a sliding scale with descriptions of compatibility. In an embodiment, a refreshment possibility may be considered not compatible 504, when it is not tolerated by a user's body. For example, a refreshment possibility that contains an ingredient that a user is highly allergic to may be considered not compatible 504. In an embodiment, a refreshment possibility may be considered moderately compatible 508 when it is tolerated by a user's body but may not contain optimal ingredients for a user. For instance and without limitation, a refreshment possibility that contains foods fried in canola oil may be considered moderately compatible 508 for a user who over-absorbs cholesterol from the diet. In an embodiment, a refreshment possibility may be considered highly compatible 512 when it is well tolerated by a user's body. For example, a refreshment possibility that contains a black bean burger topped with fresh avocado and sunflower seeds may be considered highly compatible 512 for a user with low high density lipoprotein (HDL). Referring now to FIG. 5B, refreshment possibility compatibility may be expressed on a numerical scale to describe compatibility. In an embodiment, a refreshment possibility may be considered not compatible when it is given a score of "0" as marked by character 516. In an embodiment, a refreshment possibility may be considered moderately compatible when it is given a score of "50" as marked by character 520. In an embodiment, a refreshment possibility may be considered highly compatible when it is given a score of "100" as marked by character 524. In an embodiment, compatibility may be expressed in a combination of descriptions and/or numerical values. In an embodiment, numerical values may be ranked on other scales, such as a scale from 0 to 10, or 0 to 1000. Persons skilled in the art, upon reviewing the entirety of this disclosure, will be aware of various compatibility scales that can be utilized.

Figure 6:
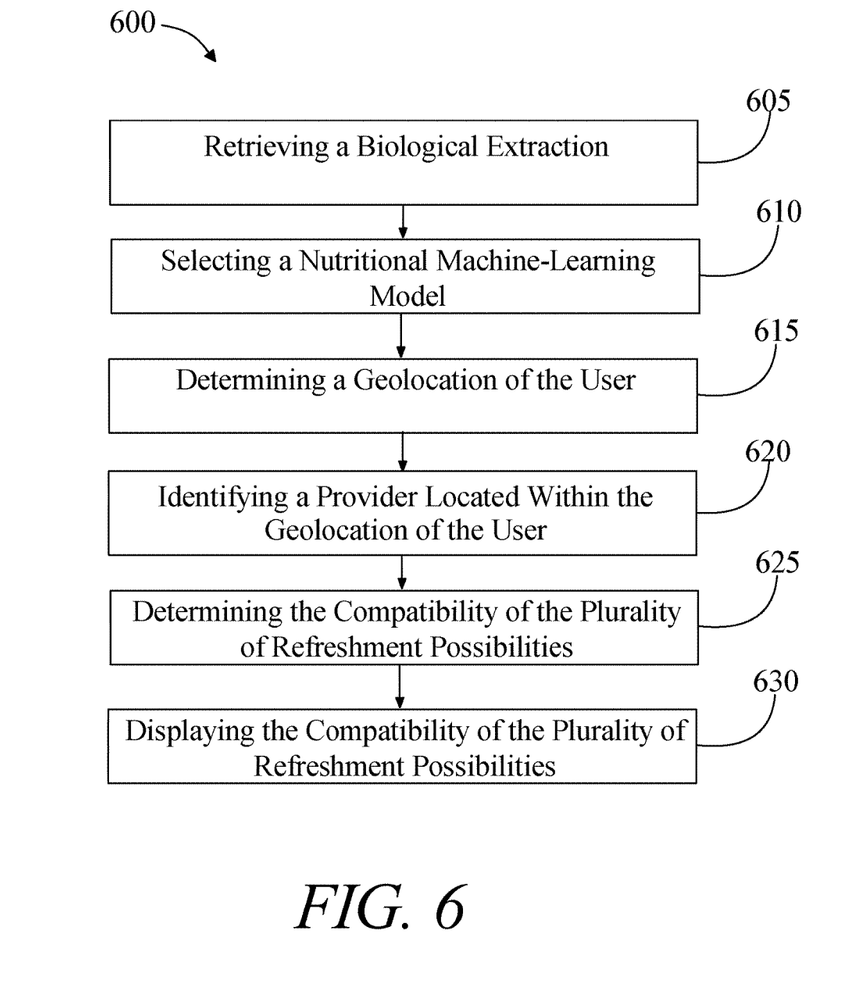
FIG. 6 is a process flow diagram illustrating an exemplary embodiment of a method of multi-factorial physiologically informed refreshment selection using artificial intelligence.

Referring now to FIG. 6, an exemplary embodiment of a method 600 of multi-factorial physiologically informed refreshment selection using artificial intelligence is illustrated. At step 605, computing device 104 retrieves a biological extraction 108 pertaining to a user. A biological extraction 108 includes any of the biological extraction 108 as described above in more detail in reference to FIG. 1. For instance and without limitation, a biological extraction 108 may include a blood sample analyzed for one or more markers of inflammation such as erythrocyte sedimentation rate (ESR), c-reactive protein (CRP), and plasma viscosity (PV). In yet another non-limiting example, a biological extraction 108 may include a questionnaire completed by a user, describing how a user feels psychologically. One or more biological extraction 108 may be stored in user database 112 as described above in more detail.

With continued reference to FIG. 6, at step 610, computing device 104 selects a nutritional machine-learning model 116 using a biological extraction 108. Nutritional machine-learning model includes any of the nutritional machine-learning model 116 as described above in more detail in reference to FIG. 1. For instance and without limitation, nutritional machine-learning model 116 may include a supervised machine-learning model such as a support vector machine, linear regression, logistic regression, naïve Bayes, linear discriminant analysis, decision tree, k-nearest neighbor, neural network, and the like. In yet another non-limiting example, nutritional machine-learning model may include an unsupervised machine-learning model such as hierarchical clustering, k-means clustering, mixture models, deep belief nets, Hebbian learning, generative adversarial networks, expectation-maximization algorithm (EM), singular value decomposition, non-negative matrix factorization, independent component analysis and the like. In yet another non-limiting example, nutritional machine-learning model 116 may include a lazy learning model such as local regression, lazy naïve Bayes, and the like. One or more nutritional machine-learning model 116 may be stored in refreshment database 140, as described above in more detail. Nutritional machine-learning model may be trained using training data 120, including any of the training data 120 as described herein. Computing device 104 utilizes a biological extraction 108 to select a nutritional machine-learning model 116. For instance and without limitation, computing device 104 utilizes a biological extraction 108 to select a nutritional machine-learning model 116 associated with the same biological extraction 108. For example, a biological extraction 108 such as a urine sample analyzed for levels of iodine may be utilized to select a nutritional machine-learning model 116 associated with urine samples analyzed for levels of iodine. Computing device 104 utilizes previous user refreshment data to select a nutritional machine-learning model 116. Previous user refreshment data includes any of the previous user refreshment data as described above in more detail in reference to FIG. 1. For instance and without limitation, previous user refreshment data may contain previous refreshment possibilities that were presented to a user. Computing device 104 utilizes such information to select a nutritional machine-learning model 116. For example, computing device 104 may utilize previous user refreshment data to examine a previous nutritional machine-learning model 116 utilized, and evaluate the previous nutritional machine-learning model 116 to determine if it can be utilized again, or if a separate nutritional machine-learning model 116 needs to be selected. In an embodiment, previous user refreshment data may be utilized as training data 120 and utilized to train nutritional machine-learning model 116.

With continued reference to FIG. 6, at step 615, computing device 104 determines a geolocation 124 of a user. A geolocation 124 of a user includes any of the geolocation 124 as described above in more detail in reference to FIG. 1. A geolocation 124 may be determined based on a global positioning system (GPS) of a user. In yet another non-limiting example, a user may enter information and transmit the information to computing device 104 detailing the user's geolocation 124 from a remote device 128 operated by the user. Remote device 128 may include any of the remote device 128 as described above in more detail in reference to FIG. 1. In an embodiment, a geolocation 124 of a user may include information describing the current location of the user. For example, a geolocation 124 may specify that a user is currently located in Honolulu, Hi. In an embodiment, a geolocation 124 of a user may include information describing a future location where a user will be located at a point in time in the future. For example, a geolocation 124 of a user may detail that a user will be located in Washington D.C. for the next three weeks. In yet another non-limiting example, a geolocation 124 of a user may detail that a user will be temporarily staying in a neighborhood in Topeka, Kans. for six weeks in the fall. Information pertaining to a user's geolocation 124 may be stored in user database 112.

With continued reference to FIG. 6, at step 620, computing device 104 identifies a provider 136 located within a geolocation of a user. A provider 136 includes any of the provider 136 as described above in more detail in reference to FIG. 1. For example, a provider 136 may include a sit down restaurant where food is served by wait staff. In yet another non-limiting example, a provider 136 may include a kitchen that prepares meals for sale. Information pertaining to location of provider 136 may be stored within refreshment database 140. Computing device 104 receives a user input containing an element of user geolocation 124 data. An element of user geolocation 124 data includes any of the elements of user geolocation 124 data as described above in more detail in reference to FIGS. 1-5. Computing device 104 utilizes an element of user geolocation 124 data to locate provider 136 within a specified distance of the element of user geolocation 124 data. Information pertaining to a specified distance of the element of user geolocation 124 data may be stored in user database 112. For instance and without limitation, a user may prefer to locate provider 136 within five miles of the user's geolocation 124. In yet another non-limiting example, a user may prefer to locate provider 136 within fifty five miles of the user's geolocation 124. A user may have a preference for provider 136 to be located within a specified distance based on the user's geolocation 124. For example, when a user is located in a Metropolitan area such as Savannah, Ga. a user may have a preference to locate provider 136 within two miles of the user's geolocation 124, while when the user is in a more rural location such as Ennis, Mont., a user may have a preference to locate provider 136 within one hundred miles of the user's geolocation 124.

With continued reference to FIG. 6, computing device 104 identifies provider 136 utilizing refreshment programs. Refreshment programs include any of the refreshment programs as described above in more detail in reference to FIG. 1. A refreshment program includes information describing particular meals that a provider 136 has available. For example, a refreshment program may indicate if a provider 136 serves breakfast, lunch, dinner, snacks, and the like. Information pertaining to refreshment programs of provider 136 may be stored in refreshment database 140. Such information may be updated in real time, to account for changes in refreshment programs that may occur. Refreshment programs may include information describing specific menu items and meals available during each meal service offered. For example, a refreshment program may detail that a provider 136 only serves dinner, and menu items for dinner include spaghetti and meatballs, pan seared cod with purple potatoes, chicken tacos, and vegetarian pasta. Computing device 104 identifies providers located within a geolocation 124 of a user based on refreshment programs. For example, a user may specify that the user is looking for provider 136 that serve afternoon tea and snacks. In such an instance, computing device 104 locates provider 136 that have afternoon tea and snacks available. In yet another non-limiting example, a user may specify that a user is looking for a certain meal or dish, such as a turkey club sandwich. In such an instance, computing device 104 identifies provider 136 that have refreshment programs that include a turkey club sandwich.

With continued reference to FIG. 6, at step 625 computing device 104 determines a compatibility of a plurality of refreshment possibilities utilizing a biological extraction 108 and a nutritional model. Compatibility includes any of the compatibility as described above in more detail in reference to FIG. 1. Compatibility includes any numerical, character, and/or symbolic data specifying how likely a refreshment possibility will be tolerated by a user's body. In an embodiment, compatibility may be represented on a scale, such as any of the scales as described above in more detail in reference to FIGS. 5A-5B. Computing device 104 determines compatibility utilizing a biological extraction 108 and nutritional model. Computing device 104 determines compatibility by utilizing a user's biological extraction 108 and a plurality of refreshment possibilities as inputs into nutritional machine-learning model 116, and outputs compatibility of the plurality of refreshment possibilities. Nutritional machine-learning model may be trained using training data 120, including any of the training data 120 as described herein. Computing device 104 determines compatibility, utilizing information regarding previous recent refreshment selections of a user. Computing device 104 retrieves a recent refreshment selection, identifying a consumed refreshment. Information pertaining to a recent refreshment selection may be stored in user database 112. A recent refreshment selection includes any of the recent refreshment selections as described above in more detail in reference to FIG. 1. Computing device 104 utilizes a recent refreshment selection to determine the compatibility of a plurality of refreshment possibilities. Computing device 104 may utilize a recent refreshment selection as an input to nutritional machine-learning model 116. For example, a recent refreshment selection may identify a meal a user recently consumed that contained fried chicken and waffles. Computing device 104 utilizes the information about the fried chicken and waffles to in combination with a user's biological extraction 108 and nutritional machine-learning model 116 to determine the compatibility of a plurality of refreshment possibilities. In such an instance, computing device 104 may rank a refreshment possibility containing fresh greens as being more highly compatible as compared to a refreshment possibility containing fried seafood.

With continued reference to FIG. 6, computing device 104 determines a compatibility of a plurality of refreshment possibilities for a first provider 136. For example, computing device 104 may locate a first provider 136 within a specified distance of a geolocation 124 of a user and determine a compatibility of a plurality of refreshment possibilities using a current refreshment program for the first provider 136. Computing device 104 utilizes the compatibility of a plurality of refreshment possibilities for a first provider 136 to determine the compatibility of a plurality of refreshment possibilities for a second provider 136. For example, computing device 104 may determine that a refreshment possibility consisting of pasta with an alfredo sauce contains too many carbohydrates for a user. In such an instance, computing device 104 may utilize the compatibility of the pasta with an alfredo sauce that contains too many carbohydrates to determine that a refreshment possibility consisting of angel hair pasta with shrimp from a second provider 136 also contains too many carbohydrates. Computing device 104 determines the compatibility of a plurality of refreshment possibilities using an ingredient list for each of the plurality of refreshment possibilities. An ingredient list includes any of the ingredient lists as described above in more detail in reference to FIG. 1. For example, an ingredient list may describe ingredients used in a refreshment possibility, that computing device 104 can analyze to determine compatibility. For example, computing device 104 may analyze a refreshment possibility that contains chicken Milanese and determine that because the chicken Milanese is cooked in butter, it is not very compatible for a user who has had a previous heart attack. In yet another non-limiting example, computing device 104 may analyze an ingredient list for lobster salad and determine that the lobster salad is compatible for a user with hypothyroidism who is following a gluten free diet, because the lobster salad does not contain any gluten. Ingredient lists may be updated in real time, on a timed interval, to account for different ingredients that may be utilized and substituted while making and preparing refreshment possibilities due to supply issues, seasonal availability of ingredients, and the like. Ingredient lists may be stored in refreshment database 140 and updated in real time utilizing any network methodology as described herein. In an embodiment, an ingredient list and/or a single ingredient may be fed into nutritional machine-learning model as an input.

With continued reference to FIG. 6, computing device 104 is configured to determine an incompatible refreshment possibility. An incompatible refreshment possibility includes any of the incompatible refreshment possibilities as described above in more detail in reference to FIG. 1. An incompatible refreshment possibility may be ranked on a scale, as described above in more detail in reference to FIGS. 5A-5B. Computing device 104 may propose a modification to a refreshment possibility to improve the compatibility. A modification includes any of the modifications as described above in more detail in reference to FIG. 1. For instance and without limitation, computing device 104 may determine a refreshment possibility such as guacamole and corn chips is not highly compatible for a user because the guacamole contains high amounts of onion and garlic, and the user is supposed to be following a low-FODMAP diet, and onion and garlic are considered high-FODMAP ingredients. In such an instance, computing device 104 may propose a modification, that specifies to eliminate the garlic and onion, and instead use garlic infused olive oil for flavor instead, thereby making the refreshment possibility more compatible for the user. In yet another non-limiting example computing device 104 may determine that a refreshment possibility that contains hot chocolate prepared with coconut milk contains too much saturated fat for a user with an apolipoprotein E 4 (APE4) genetic variant, but that the hot chocolate prepared with almond milk would be more compatible for the user. Information relating to modifications and/or substitutions may be stored in refreshment database 140. Computing device 104 determines compatibility of refreshment possibilities utilizing a user specification element. A user specification element includes any of the user specification element 152 as described above in more detail in reference to FIG. 1. For example, a user specification element may contain information describing a user's preferences regarding foods a user likes to eat, foods a user doesn't like to eat, eating habits of the user, frequency with which a user cooks meals at home versus purchasing meals to be delivered and the like. For example, computing device 104 may utilize a user specification element that details a user who does not like corn, to rank a refreshment possibility that contains corn as being much less compatible for a user, as compared to a refreshment possibility that does not contain corn. Information pertaining to a user specification element may be stored in user database 112, as described above in more detail in reference to FIG. 1.

With continued reference to FIG. 6, at step 630, computing device 104 displays a compatibility of a plurality of refreshment possibilities. Computing device 104 may display a compatibility of a plurality of refreshment possibilities on graphical user interface 132. In yet another non-limiting example, computing device 104 may transmit compatibility of a plurality of refreshment possibilities to remote device 128 operated by a user. This may be performed, utilizing any network methodology as described herein.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
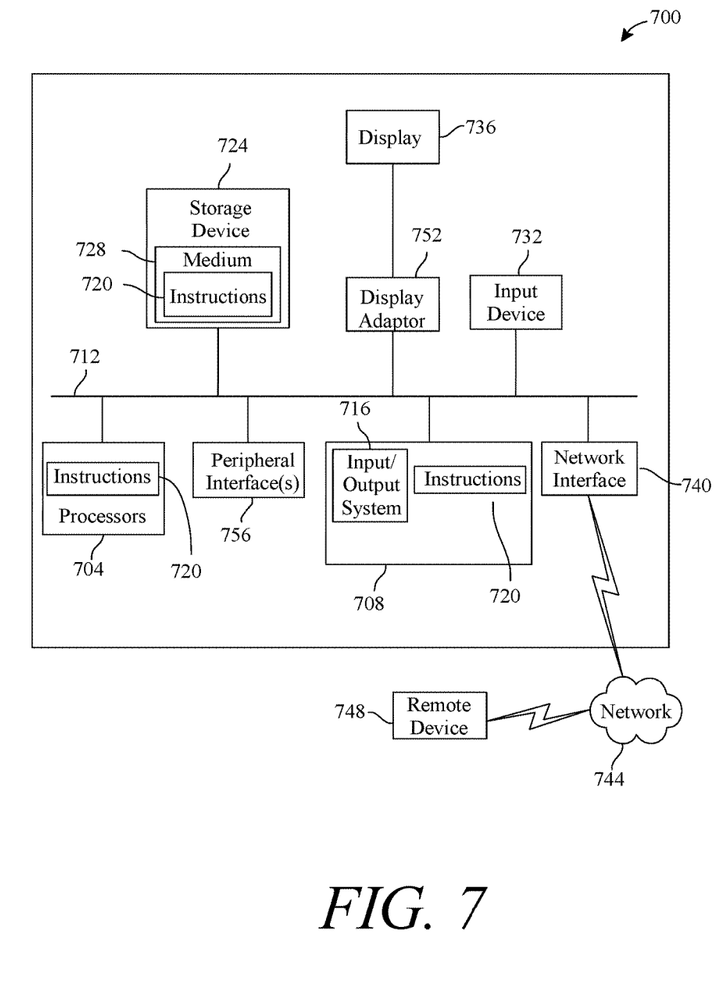
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Memory 708 may include various components (e.g., machine-readable media) including, but not limited to, a random access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIRE-WIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for multi-factorial physiologically informed refreshment selection using artificial intelligence the system comprising a computing device, the computing device designed and configured to:
   retrieve a biological extraction pertaining a user, wherein the biological extraction contains an element of user data;
   select a nutritional machine-learning model using the biological extraction;
   determine a geolocation of the user;
   identify a provider located within the geolocation of the user, wherein the provider generates a plurality of refreshment possibilities;
   determine the compatibility of the plurality of refreshment possibilities utilizing the biological extraction and the nutritional machine-learning model;
   determine an incompatible refreshment possibility;
   propose a modification to the incompatible refreshment possibility to improve the compatibility; and
   display the compatibility of the plurality of refreshment possibilities.

2. The system of claim 1, wherein the computing device is further configured to select the nutritional machine-learning model utilizing previous user refreshment data.

3. The system of claim 1, wherein the computing device is further configured to:
   receive a user input containing an element of user geolocation data; and
   locate providers located within a specified distance of the element of user geolocation data.

4. The system of claim 1, wherein the computing device is further configured to:
   identify the provider located within the geolocation of the user as a function of a refreshment program; and
   receive from the provider, the refreshment program.

5. The system of claim 1, wherein the computing device is further configured to:
   retrieve a recent refreshment selection, wherein the recent refreshment selection identifies a consumed refreshment; and
   determine the compatibility of the plurality of refreshment possibilities using the recent refreshment selection.

6. The system of claim 1, wherein the computing device is further configured to:
   determine the compatibility of the plurality of refreshment possibilities for a first provider; and
   utilize the compatibility of the plurality of refreshment possibilities for the first provider to determine the compatibility of the plurality of refreshment possibilities for a second provider.

7. The system of claim 1, wherein the computing device is further configured to determine the compatibility of the plurality of refreshment possibilities utilizing an ingredient list for each of the plurality of refreshment possibilities.

8. The system of claim 7, wherein the ingredient list is updated on a timed interval from the provider.

9. The system of claim 1, wherein the computing device is further configured to:
retrieve a user specification element; and
determine the compatibility of the plurality of refreshment possibilities using the user specification element.

10. A method of multi-factorial physiologically informed refreshment selection using artificial intelligence the method comprising:
retrieving by a computing device, a biological extraction pertaining a user, wherein the biological extraction contains an element of user data;
selecting by the computing device, a nutritional machine-learning model using the biological extraction;
determining by the computing device, a geolocation of the user;
identifying by the computing device, a provider located within the geolocation of the user, wherein the provider generates a plurality of refreshment possibilities;
determining by the computing device, the compatibility of the plurality of refreshment possibilities utilizing the biological extraction and the nutritional machine-learning model;
determining by the computing device, an incompatible refreshment possibility;
proposing by the computing device, a modification to the incompatible refreshment possibility to improve the compatibility; and
displaying by the computing device, the compatibility of the plurality of refreshment possibilities.

11. The method of claim 10, wherein selecting the nutritional machine-learning model further comprises selecting the nutritional machine-learning model utilizing previous user refreshment data.

12. The method of claim 10, wherein determining the geolocation of the user further comprises:
receiving a user input containing an element of user geolocation data; and
locating providers located within a specified distance of the element of user geolocation data.

13. The method of claim 10, wherein identifying the provider located within the geolocation further comprises:
identifying the provider located within the geolocation of the user as a function of a refreshment program; and
receiving from the provider, the current refreshment program.

14. The method of claim 10, wherein determining the compatibility of the plurality of refreshment possibilities further comprises:
retrieving a recent refreshment selection, wherein the recent refreshment selection identifies a consumed refreshment; and
determining the compatibility of the plurality of refreshment possibilities using the recent refreshment selection.

15. The method of claim 10, wherein determining the compatibility of the plurality of refreshment possibilities further comprises:
determining the compatibility of the plurality of refreshment possibilities for a first provider; and
utilizing the compatibility of the plurality of refreshment possibilities for the first provider to determine the compatibility of the plurality of refreshment possibilities for a second provider.

16. The method of claim 10, wherein determining the compatibility of the plurality of refreshment possibilities further comprises utilizing an ingredient list for each of the plurality of refreshment possibilities.

17. The method of claim 16, wherein the ingredient list is updated on a timed interval from the provider.

18. The method of claim 10, wherein determining the compatibility of the plurality of refreshment possibilities further comprises:
retrieving a user specification element; and
determining the compatibility of the plurality of refreshment possibilities using the user specification element.

19. The system of claim 1, wherein the biological extraction further comprises an element of user data indicative of a user's physiological state, wherein the physiological state includes at least an evaluation of a user's digestive system.

* * * * *